(12) United States Patent
Daniel et al.

(10) Patent No.: US 8,012,114 B2
(45) Date of Patent: Sep. 6, 2011

(54) HEMODIALYSIS UNIT COMPRISING EMERGENCY ACTIVATION MEANS

(75) Inventors: Pia Daniel, Bodman (DE); Carsten Mueller, Euerbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 580 days.

(21) Appl. No.: 11/597,539

(22) PCT Filed: May 14, 2005

(86) PCT No.: PCT/EP2005/005322
§ 371 (c)(1),
(2), (4) Date: Nov. 27, 2006

(87) PCT Pub. No.: WO2005/118024
PCT Pub. Date: Dec. 15, 2005

(65) Prior Publication Data
US 2007/0249982 A1   Oct. 25, 2007

(30) Foreign Application Priority Data
May 27, 2004   (DE) .................... 10 2004 026 561

(51) Int. Cl.
*A61M 37/00* (2006.01)
*C02F 1/44* (2006.01)

(52) U.S. Cl. ............ 604/5.04; 604/4.01; 604/5.01; 604/6.09; 604/6.11; 604/6.01; 210/645; 210/646; 210/739; 210/741

(58) Field of Classification Search .............. 604/4.01, 604/5.01, 5.04, 6.01, 6.09, 6.11; 210/645, 210/646, 739, 741
See application file for complete search history.

(56) References Cited

U.S. PATENT DOCUMENTS

| 4,267,040 | A |   | 5/1981  | Schal |
| 4,710,164 | A |   | 12/1987 | Levin et al. |
| 4,718,891 | A |   | 1/1988  | Lipps |
| 5,346,472 | A |   | 9/1994  | Keshaviah et al. |
| 5,370,123 | A | * | 12/1994 | Shinzato ............ 600/486 |
| 5,609,770 | A | * | 3/1997  | Zimmerman et al. ...... 210/739 |
| 5,620,608 | A |   | 4/1997  | Rosa et al. |
| 5,956,023 | A |   | 9/1999  | Lyle et al. |
| 6,736,789 | B1|   | 5/2004  | Spickermann |
| 2001/0007058 | A1 |  | 7/2001 | Jonsson et al. |

FOREIGN PATENT DOCUMENTS

| DE | 694 04 805 T2 | 3/1998 |
| EP | 0 311 709 A1  | 4/1989 |
| EP | 0 652 780 B1  | 5/1995 |
| EP | 0 911 044 B1  | 4/1999 |
| JP | 3128065 A     | 5/1991 |

(Continued)

*Primary Examiner* — Leslie R Deak
(74) *Attorney, Agent, or Firm* — Jacobson Holman PLLC (57) ABSTRACT

A haemodialysis device having an emergency activating function is provided. In order to avoid critical drops in blood pressure during a dialysis treatment, the emergency activating function makes it possible for the operating staff to initiate with a single control function a blood pressure measurement and a delivery of substance into the patient's blood in the event of a hypotensive episode and at the same time to have the introduction of these measures by the haemodialyser confirmed clearly through a display having an outward appearance different from that displayed during normal operations. In addition, further automatically introduced process steps can be provided. The emergency activating function speeds up the implementation of the measures to be introduced and, at the same time prevents incorrect operation and makes it possible for the operating staff to attend directly to the patient.

21 Claims, 4 Drawing Sheets

FOREIGN PATENT DOCUMENTS

| | | |
|---|---|---|
| JP | 7509645 T | 10/1995 |
| JP | 9511605 T | 11/1997 |
| WO | WO 94/27658 | 12/1994 |
| WO | WO 96/41292 | 12/1996 |

* cited by examiner

HEMODIALYSIS UNIT COMPRISING EMERGENCY ACTIVATION MEANS

This is a nationalization of PCT/EP05/005322 filed May 14, 2005 and published in German.

BACKGROUND OF THE INVENTION

1. Field of the Invention

The present invention relates to a haemodialysis device including an extracorporeal circulatory system in which blood from a patient is passed via a blood supply line to the blood chamber of a haemodialyser, which is divided into two chambers by a semi-permeable membrane, and from the blood chamber to the patient via a blood return line. The device further comprises a blood pump to supply the blood though the extracorporeal blood circulatory system, an addition unit for adding a substance to the blood of the patient, an ultra-filtration unit for withdrawing fluid from the second chamber of the dialyser, a blood pressure measuring unit for measuring the blood pressure of the patient, and a control and evaluation unit which is connected to the blood pump, the addition unit, the ultrafiltration unit and the blood pressure measuring unit. The device further includes an output unit for outputting information which is connected to the control and evaluation unit, comprising an input for inputting data and instructions which is connected to the control and evaluation unit.

2. Description of Related Art

In haemodialysis blood is removed continuously form a patient in an extracorporeal circulatory system, passed through a haemodialyser and re-infused back to the patient.

In this case, a metabolism similar to that of the kidneys is carried out. The haemodialyser consists of two chambers separated by a semi-permeable membrane, of which blood flows through one and a purifying fluid—the dialysis fluid—flows through the other. For this purpose the commercially available haemodialysers have thousands of hollow fibres whose walls are semi-permeable. The blood is passed through the interior of the hollow fibres whilst the dialysis fluid is generally fed in the opposite direction in the fibre interior intermediate space and removed.

The dialysis fluid has concentrations of blood components such as electrolytes which approximately correspond to those of a healthy person so that the corresponding concentrations in the blood can be kept at a normal level.

Substances to be removed from the blood such as creatinine or urea are not contained in the dialysis fluid whereby these can be removed from the blood merely by diffusion as a result of the concentration gradient at the membrane.

Excess water is removed from the blood by convection or ultra-filtration with the aid of a pressure gradient.

Haemodialysis devices are used to control these processes and usually also prepare the dialysis fluid from water and concentrates with the correct concentration and temperature. At the same time, these devices are increasingly in a position to take over a wide range of monitoring actions of the haemodialysis treatment in order to keep any danger to the patient as low as possible and allow countermeasures to be taken in good time in the event of complications.

Among the complications, drops in blood pressure are of particular importance. Problems of this kind arise in 40-50% of treatments. In approximately 20-30% of treatments the dialysis must be interrupted by the user and the blood pressure status of the patient restored. In this case, the user must carry out an always similar sequence of actions on the dialysis machine which binds him to exclusive operation of the dialysis machine for about 1-2 minutes instead of being able to devote himself directly to the patient.

These measures comprise a reduction in the blood flow in order to prevent arterial alarms at the blood pressure sensors in the blood supply line of the extracorporeal circulatory system, stopping ultra-filtration in order to prevent a further withdrawal of volume, starting blood pressure measurements in order to obtain the current blood pressure status of the patient and administering a substance into the patient's blood in order to increase the blood volume status of the patient. This can be achieved by increasing the concentration of a substance such as sodium chloride in the dialysis fluid, where sodium chloride enters into the blood through the membrane merely as a result of the difference in concentration without any significant displacement of volume. However, this can also be achieved by a volume infusion in the form of a bolus directly into the lines of the extracorporeal blood circulatory system or through the membrane of the dialyser.

EP 0 311 709 A1 discloses a haemodialysis device in which the blood pressure and the heart rate of a patient are continuously monitored. If the measured values lie outside certain ranges of values, the machine independently initiates countermeasures to stabilise the patient's circulation without any action by the staff. These measures comprise reducing the ultrafiltration and raising the sodium concentration in the dialysis fluid. According to the teaching of EP 0 311 709 A1, the dialysis staff should only be involved after unsuccessful, automatically initiated countermeasures.

EP 0 911 044 A1 of the applicant also has as its subject matter an automated intervention in the treatment. The blood pressure can be continuously monitored especially well using pulse wave transmission time measurements. In this case, the user can specify which measures should be introduced by the haemodialysis device when a drop in blood pressure occurs. These measures comprise lowering the temperature of the dialysis fluid, switching off the ultra-filtration, application of a bolus of sodium chloride solution and changing the composition of the dialysis fluid.

In order to avoid hypotonic phases, WO 94/27658 A1 proposes a manually actuatable device at a haemodialysis device which when actuated delivers additional sodium into the dialysis fluid.

In the case of manual interventions which are of great importance in practice as previously, several steps must frequently be instigated one after the other, as already described, which takes a certain space of time. In this case, the haemodialysis device confirms the individual measures differently, under which a clear presentation of the information and user guidance suffers.

SUMMARY OF THE INVENTION

The object of the invention is to further develop a generic medical appliance such that the user can quickly and simply operate the haemodialysis device to counteract drops in blood pressure during a haemodialysis treatment with the user at the same time receiving a clear confirmation of the measures introduced.

According to the teaching of the present invention, this object is solved by a haemodialysis device comprising an extracorporeal circulatory system in which blood from a patient is passed via a blood supply line to the blood chamber of a haemodialyser, which is divided into two chambers by a semi-permeable membrane, and from the blood chamber to the patient via a blood return line and in which the blood is conveyed through the extracorporeal blood circulatory system using a blood pump. The device includes an addition unit for adding a substance to the blood of the patient, an ultra-filtration unit for withdrawing fluid from the second chamber of the dialyser, a blood pressure measuring unit for measuring the blood pressure of the patient, a control and evaluation unit which is connected to the blood pump, the addition unit, the ultra-filtration unit and the blood pressure measuring unit, an output unit for outputting information which is connected to the control and evaluation unit, and an input unit for inputting data and instructions which is connected to the control and evaluation unit. The present invention provides that the input unit comprises an emergency activating means which, when actuated, delivers a signal to the control and evaluation unit, whereupon this requests a blood pressure measured value from the blood pressure measuring unit, instructs the addition unit to deliver the substance into- the blood in a pre-determined fashion and instructs the output unit to display status information on the addition of the substance to the blood and the blood pressure measurement in an outward appearance different from the outward appearance shown during the treatment.

Thus, in the event of concomitant effects indicative of a hypotensive episode, the invention makes it possible for the operating staff to introduce the immediately necessary measures by actuating the emergency activating means provided with a single instruction to the haemodialyis device. At the same time, it is possible for the operating staff to obtain automatic and unique confirmation of the measures introduced in that the output unit makes available status information on the steps taken, for example, on the screen of the haemodialysis device in an outward appearance deviating from the outward appearance displayed during the treatment.

As primary necessary first measures, the invention provides the initiation of a blood pressure measurement and the administration of a substance to the patient to stabilise the circulation. The widely used measurement using a cuff which can be pressurised with air and also relieved of pressure again using a control system can be used for the blood pressure measurement. Corresponding sensors can then record the pulse signals. A wide range of means are commonly known for this purpose to the person skilled in the art. Such cuffs are usually wound around the upper arm of dialysis patients so that a blood pressure measurement can be made at any time. However, other methods of measuring blood pressure can also be used.

The time delay for a cuff measurement plays a subordinate role according to the concept of the invention since the individual steps are run through automatically after the actuation of the emergency activating means and it only takes a few minutes to obtain the blood pressure measured value using the cuff.

There is fundamentally a choice to be made between two methods for administering the circulation-stabilising substance. Either the concentration of the dialysis fluid is altered via the control and evaluation unit of the haemodialysis device, wherein an increase in the sodium concentration especially comes into consideration. Or an infusion is administered into the patient's blood for which a corresponding sodium chloride solution is again suitable.

A separate infusion unit which is connected to the control and evaluation unit of the haemodialysis device can be used for the infusion. In present-day haemodialysis equipment however, it is increasingly common that this infusion solution can be prepared directly by the haemodialysis device using the dialysis fluid prepared in the device for this purpose.

Conventional haemodialysis devices provide up-to-date measured values and treatment parameters such as pump flows and treatment times, with the updating being subjected to different time cycles according to the parameters. Since the individual values can be updated without further characterisation, there is the risk that on triggering automatic processes, a user does not immediately recognise in which status the device is in. Thus, the invention additionally provides that the output unit of the haemodialysis device causes the status information on the measures introduced to be displayed in an outward appearance which differs from the usual outward appearance displayed during the treatment. The output is preferably made on a screen, which is now a commonly used component of dialysis equipment.

When displaying the blood pressure measured value, for example, this means that the value last displayed is not only simply updated but that the user can precisely identify that the measured value displayed is the measured value whose determination was triggered by actuating the emergency activating means. This takes place in an advantageous embodiment by providing a new-output window on the screen. The status information displayed can also comprise the qualitative confirmation of the measures introduced such as, for example, "blood pressure measurement initiated" or "bolus administration initiated".

In an especially advantageous embodiment the screen is configured as a touch-sensitive screen (touch screen) also as part of the input unit. The -emergency activating means can then be marked as an area on the screen with a corresponding symbol. By touching this symbol, the input unit sends the signal to the control and evaluation unit so that this can introduce corresponding measures. The different outward appearance of the status information adapted thereto can provide new input areas which make it possible for the operating staff to make further inputs.

Finally, additional measures can be set in motion by actuating the emergency activating means, such as for example a reduction or switching off the ultra-filtration or the blood supply.

In the course of the description of the invention so far, reference has been made to the importance of the invention for haemodialysis. In haemodialysis strictly speaking dialysis fluid is always introduced into the corresponding chamber of the haemodialyser. In addition to haemodialysis, however, haemofiltration and the combined use of both these methods, haemodiafiltration, are also important as blood purification methods. In haemofiltration, no dialysis fluid is supplied to the second chamber of the haemodialyser—now strictly speaking called haemofilter—but only ultrafiltrate is removed. The ultrafiltration rate is in this case far above the value which would be obtained as a result of removing the excess fluid in the patient's blood.

In this way substances to be removed are removed from the blood to an appreciable extent with the ultrafiltrate. At the same time, however, the fluid balance of the patient must be compensated which is achieved by adding a corresponding quantity of physiological substitution solution.

Thus, in haemofiltration treatment the circulatory loads are similar to those in haemodialysis. The concept of the invention can thus be transferred to a haemofiltration device in an obvious fashion. When the invention simply discusses haemodialysis in the following within the scope of the invention, haemofiltration or haemodiafiltration should thus be included in the same way. Also in the following, no distinction is made between a haemodialyser and a haemofilter. Rather, the term haemodialyser is used generally.

BRIEF DECRIPTION OF THE DRAWINGS

Further details and advantages of the invention are described in detail with reference to an exemplary embodiment shown in the drawings. In the figures.

DETAILED DECRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The fundamental structure of the haemodialysis device according to the invention is explained with reference to FIG. 1. In haemodialysis blood is supplied to a haemodialyser 1 via a blood supply line 5 in an extracorporeal circulatory system. In the haemodialyser 1 a semi-permeable membrane 2 usually executed in the form of many hollow fibres separates a first chamber 3 (blood chamber) which is part of the extracorporeal blood circulatory system, from a second chamber 4 (dialysis fluid chamber) which is part of a dialysis fluid circulatory system. Substances to be removed from the blood pass through the semi-permeable membrane 2 into the dialysis fluid and are removed by said fluid. At the same time, an excess quantity of fluid can be ultrafiltered from the blood via a pressure gradient and removed by means of the outflowing dialysis fluid. Finally, an inverse diffusion gradient can be used, for example, for sodium ions in order to transfer these substances from the dialysis fluid into the blood.

In the blood supply line 5 blood is transferred by a blood pump 6 configured as a roller pump. The blood leaves the first chamber 3 of the haemodialyser 1 via the blood return line 7 to be returned back to the patient. Provided on the blood return line 7 is a venous shut-off clamp 8 with which the return of the blood can be interrupted especially in emergencies. Such emergencies can occur, for example, if air is detected in the blood return line 7 by an air detector 9. The air detector 9 also comprises means for identifying the presence of blood in the blood return line 7.

An arterial pressure sensor 10 is provided on the blood supply line 5 and a venous pressure sensor 11 is provided on the blood return line 7.

Dialysis fluid flows through the second chamber 4 of the haemodialyser, which fluid is supplied via a dialysis fluid supply line 20 from a dialysis fluid preparation unit 24 and is removed via a dialysis fluid removal line 21 to an outflow 25. The dialysis fluid is circulated by conveying and balancing devices 22 and 23 wherein the quantity of any ultrafiltrate to be removed can be registered precisely.

The person skilled in the art has various arrangements at his disposal for implementing the conveying and balancing devices 22 and 23 so that further details are not given at this point. The same applies to the provision of dialysis fluid by the dialysis fluid preparation unit 24. As an example, reference is made to a balance chamber system such as that described in U.S. Pat. No. 4,267,040.

Numerous possibilities for the use of actuators and sensors in a haemodialysis device are also generally available to the person skilled in the art without it being necessary to go into detail here. The diagram in FIG. 1 is restricted to a few of these elements which are sufficient for explaining the invention.

The haemodialysis device is controlled and monitored by a control and evaluation unit 30. For this purpose the control and evaluation unit 30 is connected to the individual actuators and sensors of the equipment using signal leads. For the actuators and sensors shown in FIG. 1 this is indicated by reference numbers which have an apostrophe next to the reference number of the relevant actuator or sensor and which for the sake of clarity are only indicated at the control and evaluation unit 30.

The control and evaluation unit 30 is connected to an output and input unit 32 via a data link 31. The output and input unit 32 comprises a screen 33 constructed as a touch screen. Information notified by the control and evaluation unit 30 is displayed on the touch screen and at the same time, data entered by an operator via the touch screen is passed on to the control and evaluation unit 30.

A substituate line 26 which opens into the blood return line 7 branches off from the dialysis fluid supply line 20.

Provided in the substituate line 26 is a substituate pump 12 for supplying dialysis fluid as substituate into the extracorporeal circulatory system of the haemodialysis device which is controlled by the control and evaluation unit 30.

Figure 1:
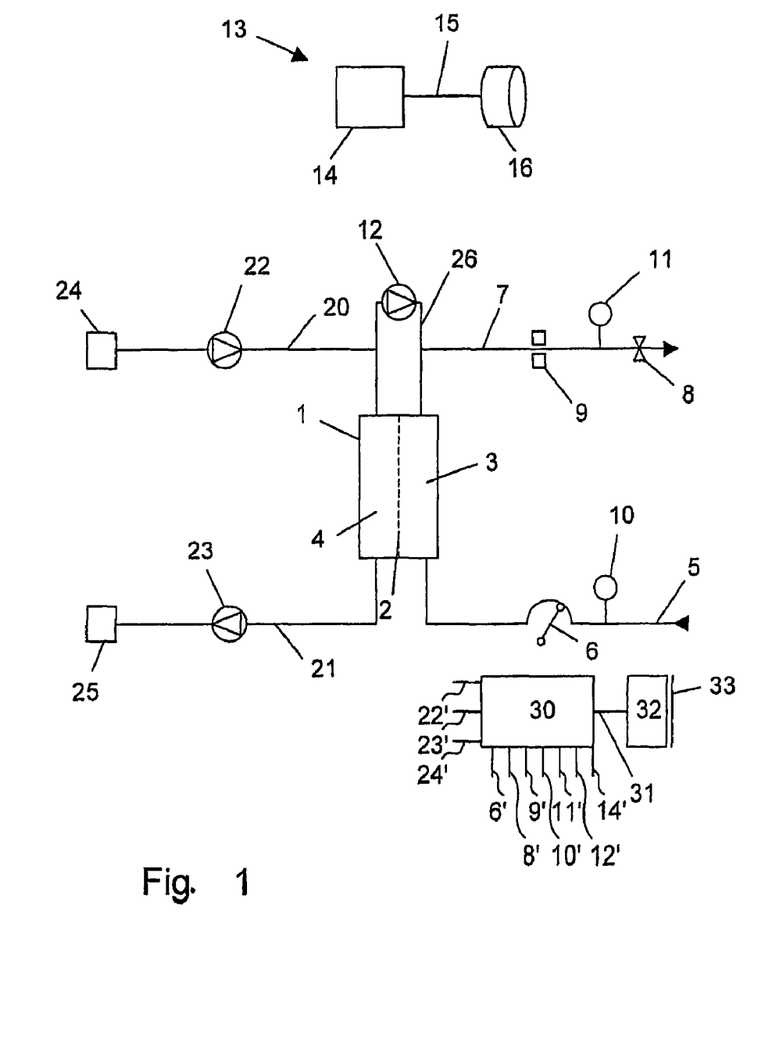
FIG. 1 is a schematic diagram of an embodiment of the haemodialysis device according to the invention.

The haemodialysis device shown in FIG. 1 can be used for pure haemodialysis by deactivating the substituate pump 12.

If the dialysis fluid line 20 is interrupted between the branch-off point of the substituate line 26 and the second chamber 4 by means of a valve not shown, a haemofiltration treatment can be carried out and with simultaneous haemodialysis and haemofiltration, a haemodiafiltration treatment can be carried out. In the dialysis fluid supply line 20 and/or the substituate line 26, filters not shown in detail can be provided for sterile filtration of the dialysis-fluid for which various solutions are available to the person skilled in the art.

A blood pressure measuring unit 13 is connected to the control and evaluation unit 30. The blood pressure measuring unit 13 consists of a control unit 14 and an inflatable cuff 16 which can be affixed to an arm of the patient and connected to the control unit 14 via a connecting line 15. The connecting line 15 comprises the air and signal lines required for the measurement so that the control unit 14 together with a compressor not shown can execute a blood pressure measurement using the Riva Rocci method. If the control and evaluation unit 30 initiates a measurement, the blood pressure measured value determined by the control unit 14 can be notified back to the control and evaluation unit 30.

Figure 2:
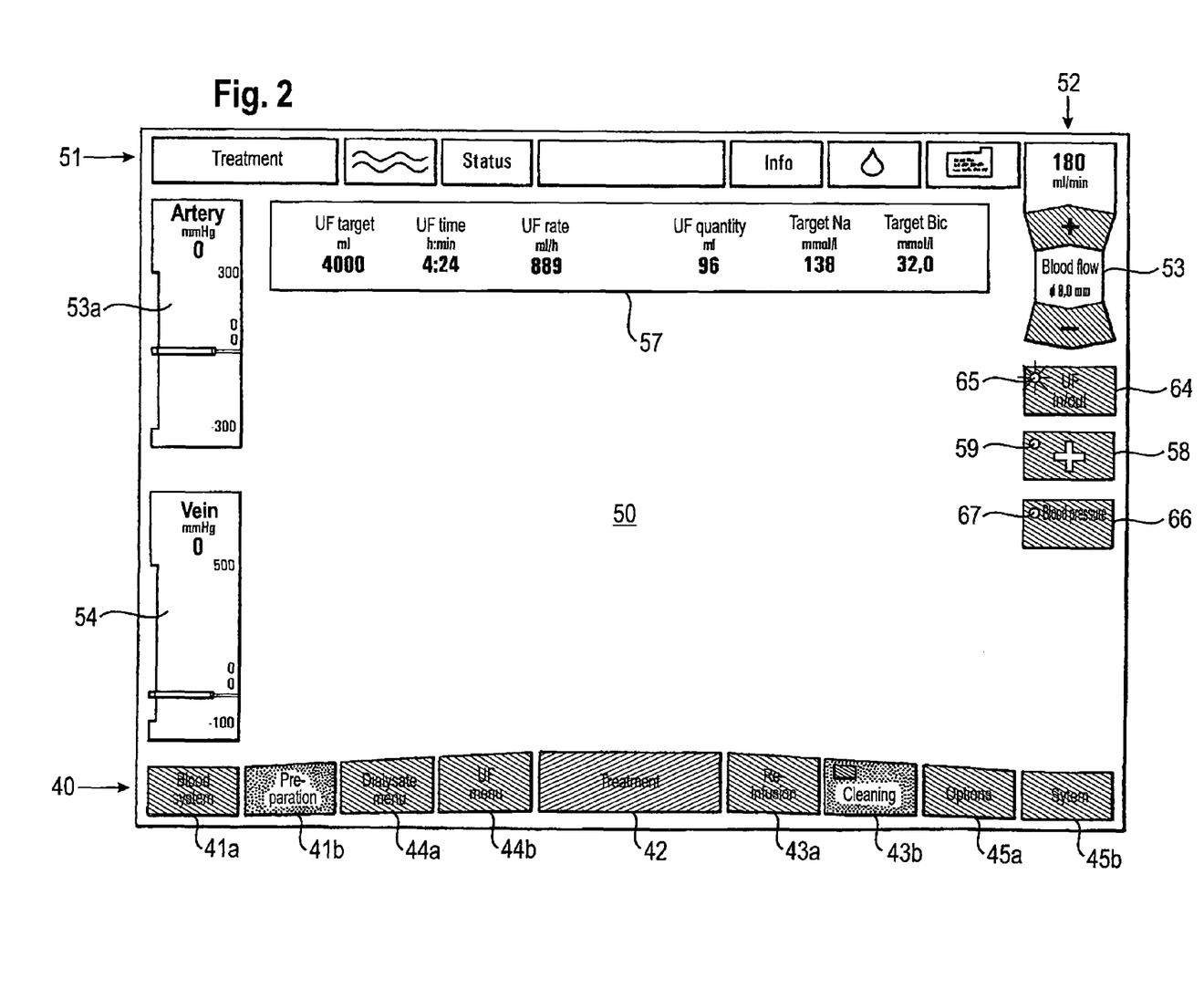
FIG. 2 is a first view shown on the screen of the haemodialysis device shown in FIG. 1 with the outward appearance shown during the treatment.

FIG. 2 shows a first view of the touch screen 33 of the haemodialysis device. At the lower edge of the touch screen are various mode means 40 in an adjacent row. The mode means 40 comprise various types of mode means. Firstly there are blood treatment preparation means 41a and 41b, blood treatment means 42 and blood treatment after-preparation means 43a and 43b, i.e., these mode means relate to time modes before a blood treatment—a haemodialysis treatment in this case—the actual blood treatment and after a blood treatment. Furthermore, supplementary mode means 44a, 44b and 45a and 45b are provided to make it possible to enter supplementary information at a plurality of time points.

Arranged on the touch screen 33 above the mode means 40 is a region 50 on which various views are to be seen according to the operating mode. In the edge regions 51, 52 further input and/or output means (for example, means 53 for the blood pump 6) are provided to make it possible to make specific data inputs and display desired information. These edge regions can have the same structure regardless of the operating mode or they can depend thereon.

The view shown in FIG. 2 shows the outward appearance in the treatment mode, that is during the actual blood treatment. In the treatment mode the data strip 57 is displayed on the display area 50. Data strip 57 gives the treatment progress parameters such as the remaining treatment time and the ultrafiltration quantity already withdrawn. Also displayed are basic values of the dialysis fluid composition such as the sodium and bicarbonate concentration. The values recorded by the pressure sensors 10 and 11 are displayed in the regions 53a and 54.

The data strip 52, which among other things contains the operating and display means 53 for the blood pump 6, also contains an emergency activating means 58. The emergency activating means 58 is provided with a symbol such as a first aid cross, for example in order to directly impart the meaning of this means to the operating staff. The entire area of the emergency activating means 58 has a part area 59 which can be displayed as, for example, dark or light underlaid, in two different outward appearances. A light form of representation confirms that the emergency activating means 58 has previously been activated and the measures and control programs introduced are still active.

Shown below the emergency activating means 58 is a blood pressure measuring means 66 which also has a part region 67 which is represented in two different outward appearance such as, for example, dark or light underlaid. A light underlay indicates that a blood pressure measurement is in progress.

By actuating the emergency activating means 58 the input and output unit 32 sends a signal to the control and evaluation unit 30. After receiving the signal, the control and evaluating unit 30 requests a blood pressure measured value from the blood pressure measuring unit 13 and instructs the dialysis fluid preparation unit 24, the conveying and balancing devices 22 and 23 and the substituate pump 12 as addition unit to deliver a pre-determined quantity of dialysis fluid to the blood at a pre-determined rate. At the same time, the input and output unit 30 is instructed to display the introduction of these measures by means of an outward appearance different to the outward appearance displayed during the treatment, comprising status information on the addition of dialysis fluid to the blood and the blood pressure measurement. For this reason after actuating the emergency activating means 58 the second view shown in FIG. 3 appears on the touch screen 33.

Inside the emergency activating means 58 there is provided an emergency program indicator 59 in the form of a simulated green light-emitting diode (LED) which suitably lights up accordingly after the emergency program has been activated. This also applies to the part region 67 in the blood pressure measuring means 66 where the illuminated part region 67 symbolises the active blood pressure measurement process. At the same time an emergency menu means 60 and a previously non-visible output window 61 are faded in. With the aid of the emergency menu means 60 it is possible to change to the view shown in FIG. 3 at any time as long as the emergency program is active. Otherwise the emergency menu means 60 is faded out again.

Figure 3:
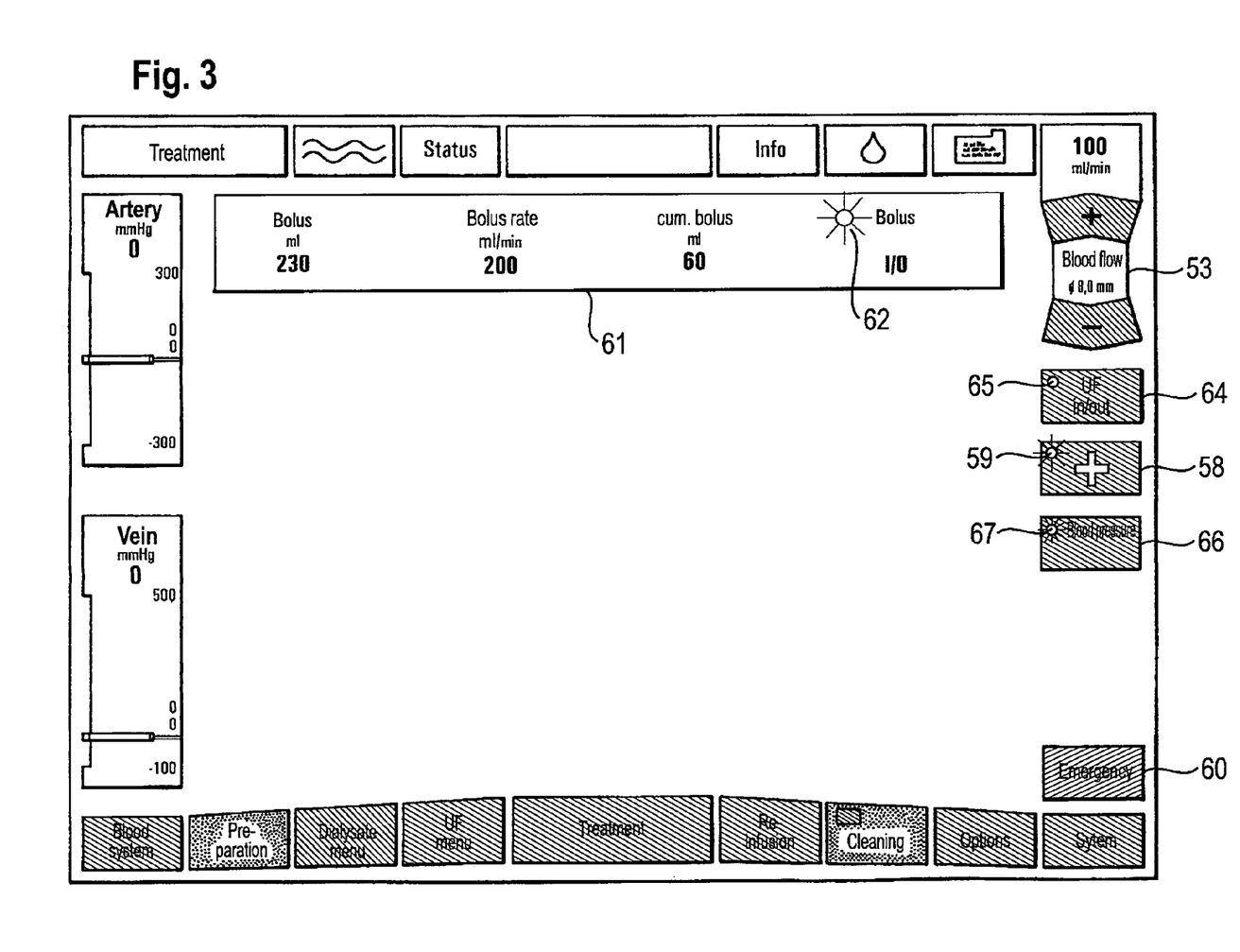
FIG. 3 is a second view shown on the screen with an outward appearance adjusted after actuating the emergency activating means and FIG. 4 is a third view shown on the screen which follows the second view with a time delay.

After actuating the emergency activating means 58 the blood treatment means 42 is shown in a different form of representation (indicated by the shading in the drawings) similar to the neighbouring mode means 43a and 44b in order to additionally symbolise that the emergency program is now active. Instead of this, the emergency menu means 60 is shown in the form of representation in which that of the blood treatment means 42 was shown in FIG. 2.

The output window 61 shows the user the status of the addition of a fluid bolus to the patient's blood. For this purpose the control and evaluation unit 30 instructs the substituate pump 12 to supply a corresponding quantity of sterile dialysis fluid to the blood return line 7. The volume quantity of the bolus, the present delivery rate of the pump 12, the quantity of the bolus already infused (cumulated bolus) and a bolus program indicator 62 (bolus I/O) again in the form of a simulated LED can be identified in the display window 61. The simulated LED 62 lights up during the running of the program to add dialysis fluid, which in particular contains sodium chloride. By actuating the indicator 62 the substance addition can be interrupted, continued or repeated at any time. Also the bolus quantity and the bolus rate setting can be provided with new values if necessary by touching the respective numerical information.

At the same time as controlling the addition unit 12, the control and evaluation unit 30 sends a signal to the blood pressure measuring unit 13 to measure the patient's blood pressure. The control unit 14 of the blood pressure measuring unit 13 then initiates inflation of the cuff 16 in order to carry out an automated blood pressure measurement on the patient. After concluding this measurement, the control unit 14 sends the data for the systolic (SYS), diastolic (DIA) and the mean arterial blood pressure (MAP) as well as the heart pulse to the control and evaluation unit 30. This sends the data to the input and output unit 32 so that information on the status of the blood pressure measurement is displayed (FIG. 4) in an outward appearance which is again modified, which appears correspondingly delayed in time as a result of the time-delayed conclusion of the blood pressure measurement.

Figure 4:
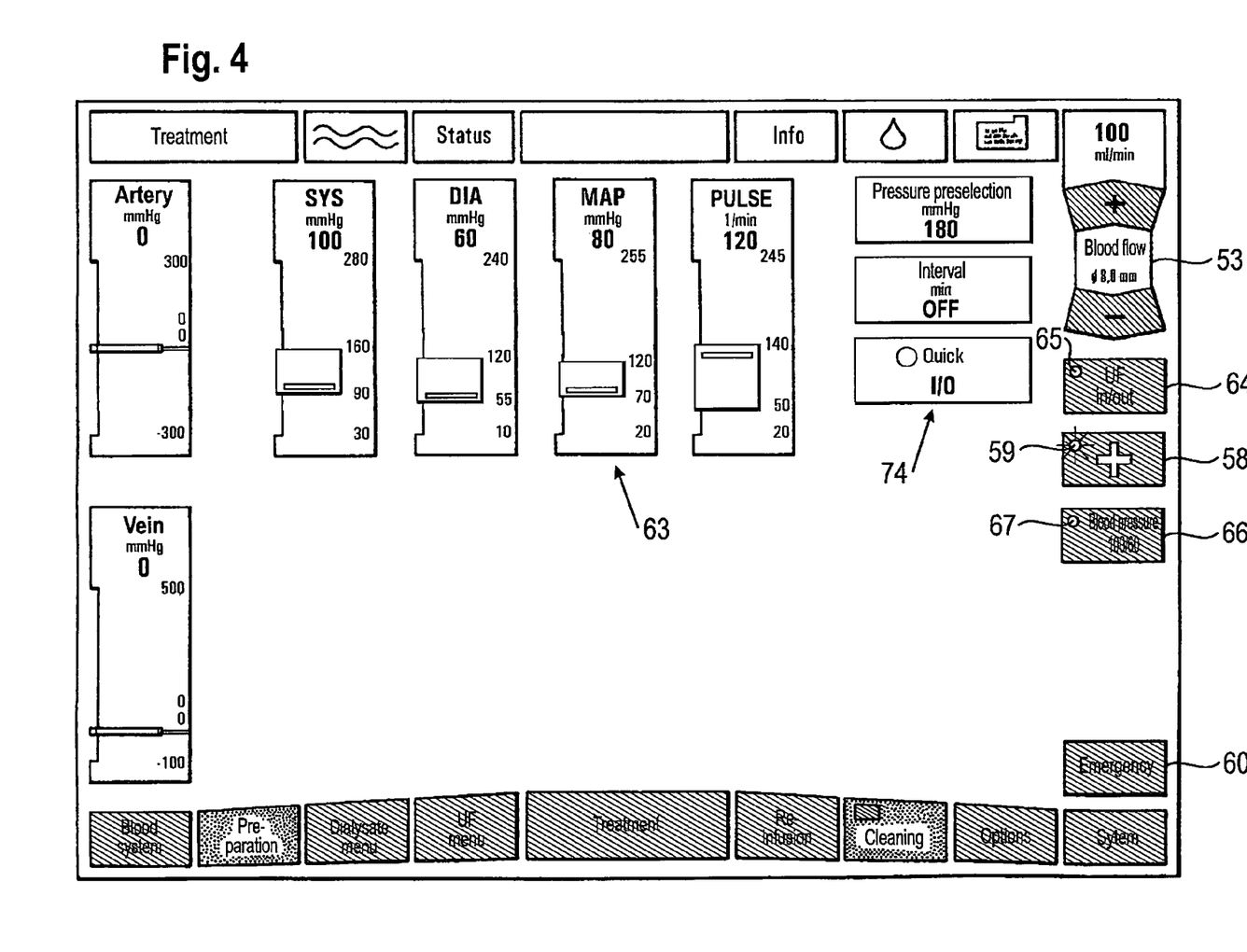

In the view shown in FIG. 4 the output window 61 is replaced by an output window 63 on which the values for the systolic (SYS), diastolic (DIA) and the mean arterial blood pressure (MAP) as well as the heart pulse are shown as numerical values and in simulated analogue displays. At the same time, means 74 are faded in with which the pressure pre-selection of the inflation pressure for the cuff, a possible automatic interval measurement of the blood pressure and an immediate re-measurement of the blood pressure via an on/off switch can be rendered possible. In the blood pressure measuring means 66 the part region 67 is again shown dark since the actual measurement process has been concluded. At the same time, the measured values for the systolic and the diastolic blood pressure are additionally displayed on the blood pressure measuring means 66. This representation is retained if other information is shown instead of the output window 63.

A renewed blood pressure measurement can be instigated at any time without introducing the complete emergency measures by actuating the blood pressure measuring means 66.

It can also be provided that the outward appearances shown in FIGS. 3 and 4 are combined, that is in particular the display windows 61 and 63 are shown in a common view.

At the same time as controlling the addition unit 12 as well as the blood pressure measuring unit 13 by the control and evaluation unit 30, after receipt of the signal from the emergency activating means 58, the control and evaluation unit 30 instructs the blood pump 6 to reduce the blood supply rate to a pre-set value. This value is automatically displayed on the means 53 for controlling the blood pump 6 (100 ml/min here).

In addition, the ultra-filtration unit 22, 23 is instructed to interrupt the ultra-filtration. This is displayed by an ultra-filtration active display means 65 again in the form of a simulated LED, which is located on an on/off switching means 64 for the ultra-filtration unit 22, 23. After pressing the emergency activating means 58, the simulated LED 65 disappears.

The emergency program which is worked through by the control and evaluation unit 30 after actuating the emergency activating means 58 can be deactivated again at any time by again actuating the emergency activating means 58. The screen view then reverts to the view in the treatment mode shown in FIG. 2 and the treatment is continued with the settings set previously. The emergency program display 59 goes out and the emergency menu means 60 is no longer shown.

It can also be provided that the emergency program again reverts automatically to the treatment mode after a set time, by setting the ultra-filtration unit 22, 23 and/or the blood pump 6 to the previous supply values. The same can occur if the on/off switching means 64 of the ultra-filtration unit 22, 23 is actuated during the emergency program. It can also be provided that the control and evaluation unit 30 gives an alarm signal after a preset time during which the emergency program is active.

Via a user configuration menu (not shown) it can be provided that the user activates or deactivates individual measures which the control and evaluation unit 30 instigates after actuation of the emergency activating means 58, or sets parameter values. In particular, it has proved advantageous if the deactivation of the ultra-filtration unit and the reduction of the blood supply rate, the level of the reduced blood supply rate as well as the individual infusion values for the substance addition such as fluid volume and supply rate can be set.

The invention makes it possible for the operating staff to initiate with a single control function important diagnostic and therapeutic measures during a haemodialysis treatment in the event of a hypotensive episode and at the same time obtain clear confirmation that these measures have been introduced by the haemodialysis device. This speeds up the implementation of the measures to be introduced and at the same time reduces incorrect operations which should be avoided at all costs when circulatory problems of patients become apparent.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A haemodialysis device including an extracorporeal circulatory system in which blood from a patient is passed via a blood supply line to the blood chamber of a haemodialyser, which is divided into two chambers by a semi-permeable membrane, and from the blood chamber to the patient via a blood return line and comprising a blood pump to supply the blood through the extracorporeal blood circulatory system, comprising:
   an addition unit configured to add a substance to stabilize the circulation to the blood of the patient,
   an ultra-filtration unit configured to withdraw fluid from the second chamber of the dialyser,
   a blood pressure measuring unit configured to measure the blood pressure of the patient,
   a control and evaluation unit which is connected to the blood pump, the addition unit, the ultrafiltration unit and the blood pressure measuring unit,
   an output unit configured to output information which is connected to the control and evaluation unit, and
   an input unit configured to input data and instructions which is connected to the control and evaluation unit, said input unit including an emergency activating function which, when actuated by a single instruction, is configured to deliver a signal to the control and evaluation unit, said control and evaluation unit being programmed to automatically request a blood pressure measured value from the blood pressure measuring unit, automatically instruct the addition unit to deliver the circulation-stabilizing substance into the blood in a pre-determined fashion and automatically instruct the output unit to display status information on the addition of the circulation-stabilizing substance to the blood and the blood pressure measurement on a display in a configuration having an outward appearance different from an outward appearance shown on the display during haemodialysis treatment when the emergency activating function has not been actuated.

2. The haemodialysis device according to claim 1, wherein a dialysis fluid supply line leading from a dialysis fluid preparation unit is connected to the second chamber of the haemodialyser for the supply of dialysis fluid.

3. The haemodialysis device according to claim 2, wherein the dialysis fluid preparation unit is connected to the control and evaluation unit.

4. The haemodialysis device according to claim 3, wherein the dialysis fluid preparation unit is a part of the addition unit.

5. The haemodialysis device according to claim 4, wherein the circulation-stabilizing substance is supplied to the blood via the semi-permeable membrane of the haemodialyser.

6. The haemodialysis device according to claim 4, wherein the circulation-stabilizing substance is supplied via a substituate line which is connected to the dialysis fluid preparation unit and the blood supply line or the blood return line.

7. The haemodialysis device according to claim 1, wherein the information-outputting part of the output unit is implemented as a screen.

8. The haemodialysis device according to claim 7, wherein the screen is constructed as a touch-sensitive screen.

9. The haemodialysis device according to claim 8, wherein the emergency activating means is an area on the screen designated by a characteristic symbol whose contact results in the emission of a signal.

10. The haemodialysis device according to claim 7, wherein after receipt of the signal, the control and evaluation unit is configured to leave the output unit to make visible a previously non-visible output window for the simultaneous or subsequent display of the status information on the blood pressure measurement and substance addition on the screen.

11. The haemodialysis device according to claim 1, wherein after receipt of the signal the control and evaluation unit is configured to instruct the ultra-filtration unit to reduce the ultra-filtration to a pre-determined reduced ultra-filtration rate value.

12. The haemodialysis device according to claim 11, wherein the reduced ultra-filtration rate value is zero.

13. The haemodialysis device according to claim 11, wherein the input unit is configured to enable the user, via the input unit, to activate or deactivate the possibility of the control and evaluation unit reducing the ultra-filtration on receipt of the signal.

14. The haemodialysis device according to claim 13, wherein the input unit is configured to enable the user to pre-determine the reduced ultra-filtration rate value via the input unit.

15. The haemodialysis device according to claim 13, wherein on receipt of the signal, the control and evaluation unit in configured to instruct the output unit to display status information on the reduction of the ultra-filtration.

16. The haemodialysis device according to claim 15, wherein after receipt of the signal, the control and evaluation unit is configured to leave the output unit to make visible the status information on the reduction of the ultra-filtration on the screen in a previously non-visible output window.

17. The haemodialysis device according to claim 1, wherein after receipt of the signal, the control and evaluation unit is configured to instruct blood pump to reduce the blood supply rate to a reduced blood supply rate value.

18. The haemodialysis device according to claim 17, wherein the input device is configured to enable the user, via the input device, to activate and deactivate the possibility of the control and evaluation unit reducing the blood supply rate on receipt of the signal.

19. The haemodialysis device according to claim 18, wherein the input unit is configured to enable the user to pre-determine the reduced blood supply rate.

20. The haemodialysis device according to claim 17, wherein on receipt of the signal the control and evaluation unit is configured to instruct the output unit to display status information on the reduction of the blood supply rate.

21. The haemodialysis device according to claim 20, wherein after receipt of the signal, the control and evaluation unit is configured to leave the output unit to make visible status information on the reduction of the blood supply rate on the screen in a previously non-visible output window.

* * * * *